(12) United States Patent
Castro et al.

(10) Patent No.: US 6,648,638 B2
(45) Date of Patent: Nov. 18, 2003

(54) ORTHODONTIC APPLIANCES INCLUDING POLYCRYSTALLINE ALUMINA-BASED CERAMIC MATERIAL, KITS, AND METHODS

(75) Inventors: Darren T. Castro, Woodbury, MN (US); Richard P. Rusin, Woodbury, MN (US); William E. Wyllie, II, Sierra Madre, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 10/034,997

(22) Filed: Dec. 28, 2001

(65) Prior Publication Data

US 2003/0165790 A1 Sep. 4, 2003

(51) Int. Cl.$^7$ ................................................. A61C 3/00
(52) U.S. Cl. .......................................................... 433/8
(58) Field of Search ....................................... 433/2–24

(56) References Cited

U.S. PATENT DOCUMENTS

| | | |
|---|---|---|
| 2,926,422 A | 3/1960 | Wallshein |
| 3,026,210 A | 3/1962 | Coble |
| 3,181,240 A | 5/1965 | Kerhart et al. |

(List continued on next page.)

FOREIGN PATENT DOCUMENTS

| | | |
|---|---|---|
| DE | 1 228 754 | 6/1967 |
| DE | 1 541 219 | 1/1970 |
| DE | 2 328 213 | 1/1974 |
| DE | 25 54 145 | 6/1977 |
| EP | 0 160 481 B2 | 11/1985 |
| EP | 0 161 831 B1 | 11/1985 |
| EP | 0 284 418 B1 | 3/1988 |
| EP | 0 430 654 B1 | 11/1990 |
| EP | 1 070 484 A2 | 1/2001 |
| WO | WO 89/08085 | 9/1989 |
| WO | WO 93/07830 A1 | 4/1993 |
| WO | WO 01/15620 A1 | 3/2001 |

OTHER PUBLICATIONS

American Society of Testing Materials, "ASTM–D2805–95, Standard Test Methods for Hiding Power of Paints by Reflectometry," *Annual Book of ASTM Standards*, pp. 307–311 (1995).

American Society of Testing Materials, "ASTM–E384–99, Test Methods for Microhardness of Materials," *Annual Book of ASTM Standards*, pp. 409–432 (1999).

Bruch, "Preparation of Translucent Alumina From Powder," pp. 1–19.

Carniglia, "Reexamination of Experimental Strength–vs–Grain Size Data for Ceramics," *Journal of American Ceramic Society*, 1972; vol. 55, Issue 5: pp. 243–249.

Din En 1184 "Materials and Articles in Contact with Foodstuffs: Test Methods for Translucency of Ceramic Articles" (Aug., 1997).

Ishitobi, et al., "Fabrication of Translucent $Al_2O_3$ by High Pressure Sintering," *Ceramic Bulletin*, 1977; vol. 56, No. 6: pp. 556–558.

Jacobson, "Fracture Characteristics, Hardness, and Grain Size of Five Polycrystalline Alumina Orthodontic Brackets," Thesis Abstract, *American Journal of Orthodontics and Dentofacial Orthopedics*, Jul., 2001; vol. 120, Issue 1, pp. 92–93.

Jeppesen, "Some Optical, Thermo–Optical, and Piezo–Optical Properties of Synthetic Sapphire," *Journal of the Optical Society of America*, 1958; vol. 48, No. 9: pp. 629–632.

(List continued on next page.)

*Primary Examiner*—Cary E. O'Connor
(74) *Attorney, Agent, or Firm*—James D. Christoff

(57) ABSTRACT

An orthodontic appliance that includes a polycrystalline translucent aluminum oxide ceramic material having an average grain size of no greater than 1.0 micron and a Contrast Ratio value of less than about 0.7.

16 Claims, 8 Drawing Sheets

U.S. PATENT DOCUMENTS

| | | | |
|---|---|---|---|
| 3,423,833 A | 1/1969 | Pearlman | |
| 3,464,837 A | 9/1969 | McLean et al. | |
| 3,541,688 A | 11/1970 | McLean et al. | |
| 3,578,744 A | 5/1971 | Wildman | |
| 3,732,087 A | 5/1973 | Grossman | |
| 3,842,503 A | 10/1974 | Wildman | |
| RE28,889 E | 7/1976 | Wildman | |
| 4,097,935 A | 7/1978 | Jarcho | |
| 4,216,583 A | 8/1980 | Reynolds | 433/9 |
| 4,219,617 A | 8/1980 | Wallshein | 433/8 |
| 4,264,541 A | 4/1981 | Oda et al. | 264/62 |
| 4,285,732 A | 8/1981 | Charles et al. | 106/57 |
| 4,310,306 A | 1/1982 | Wallshein | 433/14 |
| 4,321,042 A | 3/1982 | Scheicher | 433/201 |
| 4,322,206 A | 3/1982 | Reynolds | 433/9 |
| 4,431,420 A | 2/1984 | Adair | 433/199 |
| 4,460,336 A | 7/1984 | Smith et al. | 433/9 |
| 4,544,359 A | 10/1985 | Waknine | 523/115 |
| 4,575,805 A | 3/1986 | Moermann et al. | |
| 4,595,598 A | 6/1986 | De Luca et al. | 427/2 |
| 4,681,538 A | 7/1987 | DeLuca et al. | 433/9 |
| 4,797,238 A | 1/1989 | Rhodes et al. | 264/65 |
| 4,837,732 A | 6/1989 | Brandestini et al. | |
| 4,878,840 A | 11/1989 | Reynolds | 433/9 |
| 4,927,361 A | 5/1990 | Smith et al. | 433/9 |
| 4,954,080 A | 9/1990 | Kelly et al. | 433/8 |
| 4,968,459 A | 11/1990 | Sernetz | 264/63 |
| 4,988,293 A | 1/1991 | Collins | |
| 5,011,403 A | 4/1991 | Sadoun et al. | 433/8 |
| 5,066,225 A | 11/1991 | Forbes Jones et al. | 433/8 |
| 5,096,862 A | 3/1992 | Mathers et al. | 501/98 |
| 5,231,062 A | 7/1993 | Mathers et al. | 501/96 |
| 5,242,298 A | 9/1993 | Sernetz | 433/2 |
| 5,244,849 A | 9/1993 | Roy et al. | 501/120 |
| 5,358,402 A | 10/1994 | Reed et al. | 433/8 |
| 5,376,606 A | 12/1994 | Kim et al. | 501/153 |
| 5,380,196 A | 1/1995 | Kelly et al. | 433/8 |
| 5,382,556 A | 1/1995 | Takahashi et al. | 501/153 |
| 5,439,379 A | 8/1995 | Hansen | 433/8 |
| 5,441,408 A | 8/1995 | Moschik | 433/9 |
| 5,587,346 A | 12/1996 | Zuk | 501/152 |
| 5,627,116 A | 5/1997 | Zuk | 501/119 |

OTHER PUBLICATIONS

Lynch, "Table 3–2 –Physical, Mechanical, Thermal, and Electrical Properties of Alumina," *Chemical Rubber Company Handbook of Materials Science*, 1974, pp. 358–361.

Malitson, "Refraction and Dispersion of Synthetic Sapphire," *Journal of the Optical Society of America*, 1962; vol. 52, No. 12: pp. 1377–1379.

Mendelson, "Average Grain Size in Polycrystalline Ceramics," *Journal of American Ceramic Society*, 1969; vol. 52, Issue 8: pp. 443–446.

Mizuta, "Preparation of High–Strength and Translucent Alumina by Hot Isostatic Pressing," *Journal of American Ceramic Society*, 1992; vol. 75, Issue 2: pp. 469–473.

Passmore, et al., "Strength–Grain Size–Porosity Relations in Alumina," *Journal of American Ceramic Society*, 1965; vol. 48, Issue 1: pp. 1–7.

Pham, "Fracture Characteristics, Hardness, and Grain Size of Five Polycrystalline Alumina Orthodontic Brackets," Master's Thesis, The Ohio State University, Columbus, Ohio, Title Page, Abstract, Table of Contents, pp. 1–47, (1999).

Rhodes, et al., "Hot–Working of Aluminum Oxide: II, Optical Properties," *Journal of American Ceramic Society*, 1974; vol. 58, No. 1–2: pp. 31–34.

Rhodes, et al., "Segregation of Magnesium to the Internal Surface of Residual Pores in Translucent Polycrystalline Alumina," *Journal of American Ceramic Society*, 1992; vol. 75, Issue 7: pp. 1796–1800.

Rhodes, et al., "Sintering of Translucent Alumina in a Nitrogen–Hydrogen Gas Atmosphere," *Journal of American Ceramic Society*, 2000; vol. 83, Issue 7: pp. 1641–1648.

Van Vlack, "Elements of Materials Science and Engineering," $6^{th}$ Edition, pp. 217–219, 1989.

ORTHODONTIC APPLIANCES INCLUDING POLYCRYSTALLINE ALUMINA-BASED CERAMIC MATERIAL, KITS, AND METHODS

FIELD OF THE INVENTION

This invention relates to orthodontic appliances, particularly to orthodontic appliances that include a polycrystalline alumina-based ceramic material that has a relatively small grain size yet generally high translucency.

BACKGROUND

Although performance and durability are highly desirable characteristics of orthodontic brackets, for example, they alone are not the sole concern for practitioners and patients. Aesthetic value, or how orthodontic materials look inside the mouth is just as desirable.

For orthodontic devices (typically, brackets, which are small slotted bodies for holding a curved arch wire, and associated tooth bands if banded attachment is used), stainless steel is an ideal material because it is strong, nonabsorbent, weldable, and relatively easy to form and machine. A significant drawback of metal appliances, however, relates to cosmetic appearance when the patient smiles. Adults and older children undergoing orthodontic treatment are often embarrassed by the "metallic smile" appearance of metal bands and brackets, and this problem has led to various improvements in recent years.

One area of improvement involves use of nonmetal materials. Both plastic and ceramic materials present an improved appearance in the mouth, and often the only significantly visible metal components are thin arch wires that are cosmetically acceptable. Plastic is not an ideal material because it lacks the structural strength of metal, and is susceptible to staining and other problems. Ceramics such as sapphire or other transparent crystalline materials have undesirable prismatic effects. Also, single crystal aluminum oxide appliances are subject to cleavage under the loads that occur in the course of orthodontic treatment. Other ceramics have been largely opaque so that they either do not match tooth color or require coloring.

U.S. Pat. No. 4,954,080 (Kelly et al.) describes orthodontic appliances made from a polycrystalline ceramic material such as alumina. The ceramic material of the appliances described in this patent transmits sufficient light to enable the appliance to pick up the color of the tooth. While the appliances described are considered satisfactory, there is a need in the art for orthodontic appliances made of a ceramic material that is stronger. In such an appliance, it would also be advantageous to have a material with no pre-determined color and the ability to blend with or color-match the adjacent dentition.

SUMMARY OF THE INVENTION

The present invention is directed to orthodontic appliances that include a polycrystalline ceramic material that has a desirable translucent quality. This is particularly advantageous for use in orthodontic appliances to achieve further cosmetic improvement by having a translucent quality that picks up the color of the underlying tooth to make the orthodontic appliance blend with the tooth. Preferably, the material has a Contrast Ratio value of less than about 0.7.

The polycrystalline translucent ceramic material is formed by pressing a powder material, such as high purity aluminum oxide, into a desired shape, sintering the shaped material to provide closed porosity, and subjecting the sintered material to hot isostatic pressing to yield a single phase material having substantially zero porosity and an average grain size of no greater than 1.0 micrometer (i.e., micron). This small grain size contributes to a stronger material than conventional ceramic materials without detrimentally effecting translucency. This is surprising as small grain size is often considered to prevent relatively high translucency. Preferably, the material has a flexure strength of at least about 400 MPa.

Thus, in one embodiment the present invention provides an orthodontic appliance that includes a polycrystalline translucent aluminum oxide ceramic material having an average grain size of no greater than 1.0 micron and a Contrast Ratio value of less than about 0.7.

The present invention also provides a kit that includes a plurality of orthodontic appliances, wherein at least one of the appliances includes a polycrystalline translucent aluminum oxide ceramic material having an average grain size of no greater than 1.0 micron and a Contrast Ratio value of less than about 0.7. The kit preferably further includes a component selected from the group consisting of an orthodontic adhesive, an adhesive primer, an appliance positioning tool, and combinations thereof.

The present invention also provides a method for making an orthodontic appliance or appliance perform that includes a polycrystalline translucent aluminum oxide ceramic material having a grain size of no greater than 1.0 micron and a Contrast Ratio value of less than about 0.7. The method includes: providing an aluminum oxide powder; forming the powder into an article having a desired shape; sintering the shaped article to obtain a sintered article having closed porosity; and subjecting the sintered article to hot isostatic pressing to further densify and form an orthodontic appliance or appliance perform comprising polycrystalline translucent aluminum oxide ceramic material having a grain size of no greater than 1.0 micron and a Contrast Ratio value of less than about 0.7. The method preferably further includes deagglomerating the aluminum oxide powder prior to forming the powder into an article having a desired shape. This is preferably accomplished by subjecting the aluminum oxide powder to ultra-sonication.

BRIEF DESCRIPTION OF THE DRAWINGS

Those skilled in the art may recognize that various modifications and additions may be employed in connection with the specific, presently preferred embodiments described and illustrated below in the accompanying drawings. As such, the invention should not be deemed limited to the particular embodiments set out in detail, but instead only by a fair scope of the claims that follow along with their equivalents.

DETAILED DESCRIPTION OF PREFERRED EMBODIMENTS

Figure 1:
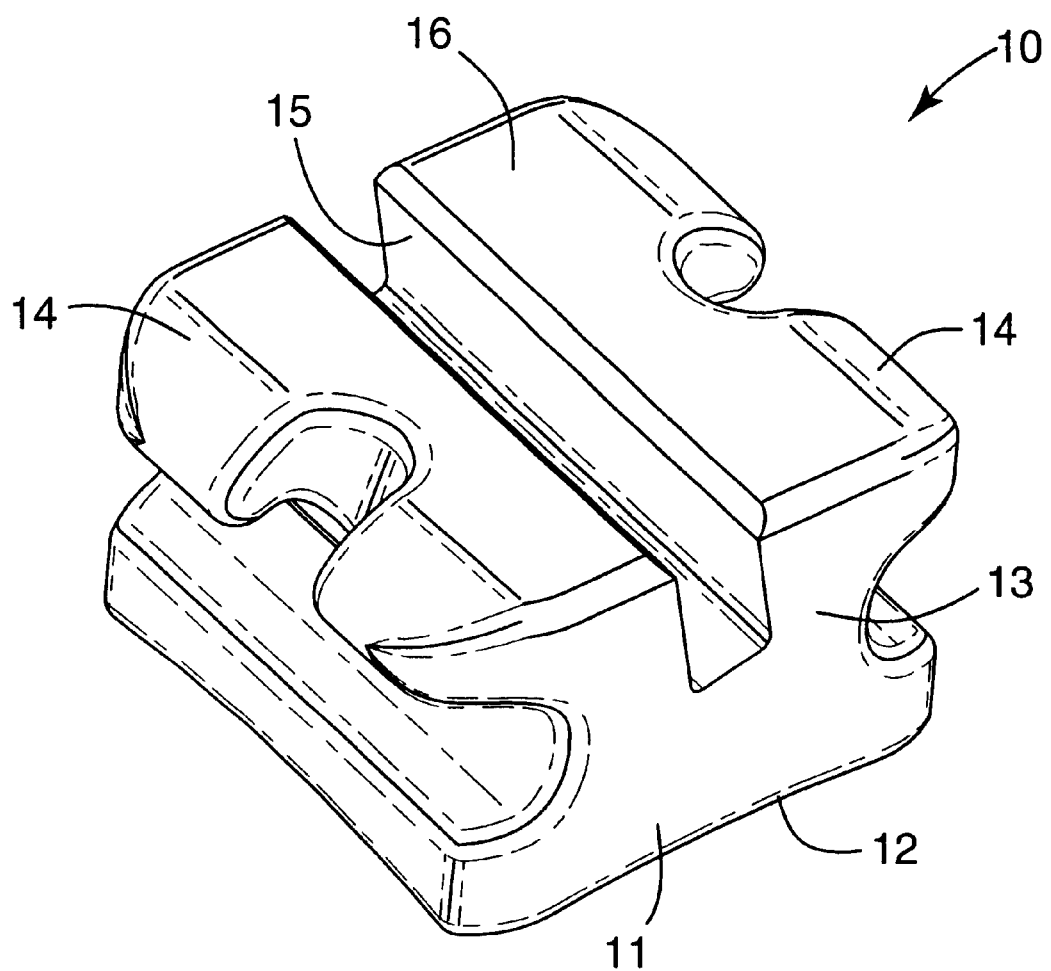
FIG. 1 is a pictorial view of an orthodontic bracket according to one embodiment of the invention.

The present invention is directed to an orthodontic appliance that includes a polycrystalline aluminum oxide ceramic material that has an average grain size of no greater than 1.0 micrometer (i.e., micron). This small grain size contributes to a stronger material than conventional ceramic materials without detrimentally affecting translucency. As a result of the high strength and translucency, the material of the present invention is particularly advantageous for use in orthodontic appliances.

Ceramic Material

The ceramic material of the present invention is a translucent polycrystalline material. A "ceramic" refers to an inorganic nonmetallic material and "crystalline" refers to material that shows crystalline diffraction peaks when subjected to a bulk powder x-ray diffraction scan and is essentially free of glass. A polycrystalline material has a multiplicity of randomly oriented crystals joined at grain boundaries. Preferably, the ceramic material includes at least 99% polycrystalline ceramic having at least 99% theoretical density.

The ceramic for the present invention is aluminum oxide. Aluminum oxide is desirable since it is strong, hard, colorless, and readily available. It is desirable that the aluminum oxide be relatively high purity (preferably at least about 99.5% pure and more preferably at least about 99.9% pure) for generally high strength and significant freedom from chromatic effects.

Preferably, the ceramic material of the orthodontic appliances of the present invention is substantially nonporous to maintain a high degree of optical translucency. Furthermore, it is preferred that the average grain size of the ceramic material be no greater than 1.0 micrometer (i.e., micron). Preferably, no greater than 10% (i.e., number percent) of the grains as measured on a polished, etched surface of the material has a largest dimension (not actual grain size) greater than 1.0 micron. Preferably, no greater than 20% (i.e., number percent) of the grains as measured on a polished, etched surface of the material has a largest dimension greater than 0.9 micron.

This is significant because most conventional ceramic orthodontic appliances have a significantly larger average grain size (e.g., 10–50 microns) and/or a significantly larger amount (e.g., 50–90%) of the grains as measured on a polished, etched surface having a largest dimension (not actual grain size) of greater than 0.8 micron. The smaller grain size of the polycrystalline material of the orthodontic appliances of the present invention contributes to the significant strength of the material without detrimentally affecting the translucency.

Thus, the ceramic material of the orthodontic appliances of the present invention is translucent. Translucency is the property of a specimen by which it transmits light diffusely without permitting a clear view of objects beyond the specimen and not in contact with it.

A translucent material is an advantage because an orthodontic appliance formed from such a material effectively blends in with its surroundings and assumes the color of the underlying teeth. This can provide improved aesthetics as compared to more opaque materials. That is, an orthodontic appliance would be more aesthetically pleasing if it were nearly indistinguishable and unnoticeable. Particularly desirable materials should be neutral, and neither add color to the light passing through nor subtract color by appreciable absorption.

The ceramic material of the present invention is preferably an alpha aluminum oxide. Aluminum oxide is particularly desirable since its optical transmittance is substantially constant throughout the visible spectrum and it therefore does not change the color of light passing through.

In order for the orthodontic appliance to assume the color of the underlying tooth, it is important that sufficient light seen from the front surface of the appliance attached to the tooth be light that has been transmitted from the tooth surface, and that the tooth color is not overwhelmed by light backscattered from optical irregularities within the appliance. In other words, a substantial amount of the incident light should pass through the appliance, albeit diffused, to the base for reflection off of the tooth surface, and then be retransmitted through the appliance to be emitted from the front surface. Since the appliance is translucent rather than transparent, a portion of the light is backscattered by the internal grain boundaries of the ceramic as well as by impurities in the article. The backscattering due to impurities is preferably minimized since such backscattered light tends to be white and will almost invariably be different from the tooth color. Further, by using a translucent ceramic material, many of the optical properties of the tooth are mimicked.

It is significant that the translucence be a bulk property of the material rather than a surface effect. Some light diffusion can be obtained by roughening a surface as, for example, with frosted glass. This is not completely satisfactory in an orthodontic appliance, however, since the surface is continually wet, and the principal change in the index of refraction occurs at the air-liquid interface, which is nearly smooth. Further, it is undesirable to have roughened surfaces on orthodontic appliances, which can provide a site for the build-up of plaque. Also, rough surfaces may also have imperfections, which serve as a source for initiation of cracks. Since ceramics do not have the ductility of metals, roughness can significantly degrade strength.

The Contrast Ratio value of a material is a measure of the opacity of the material as a ratio of the reflectance through the material on a black substrate to that of an identical material on a white substrate. Contrast Ratio values can be measured using a technique based on Section 3.2.1 of ASTM-D2805-95, modified for samples of about 1 millimeter (mm) thick. This test method is provided below. Lower values of Contrast Ratio indicate greater levels of light transmissivity.

Ceramic materials used in the orthodontic appliances of the present invention have a Contrast Ratio value less than about 0.7, preferably less than about 0.6, even more preferably less than about 0.5, and most preferably less than about 0.4.

The transmittance of a material is a measure of the opacity of the material as a percentage of light at a particular wavelength that passes through the material. Percent transmittance can be measured using a technique based on the published standard method DIN EN 1184, modified for samples of about 1 millimeter (mm) thick. The samples can be evaluated wet or dry. This test method is provided in the Examples Section.

Ceramic materials, and articles made from such materials, according to the present invention preferably have a wet transmittance of at least about 40% at about 550 nm. More preferably, the wet transmittance is at least about 50% at about 650 nm. Alternatively stated, the wet transmittance curve over a range of about 475 nm to about 650 nm has an integrated area of greater than about 70% T-nm (i.e., units of % Transmittance×Wavelength (nm)).

The ceramic material used in the orthodontic appliances of the present invention also offers other desirable properties such as high flexure strength. Flexure strength can be measured according to the test methods described in the Examples Section. It is desirable that the material of an orthodontic appliance has high strength and reliable mechanical properties when machined into a complex shape and subjected to complex stresses. For example, point sources of very high magnitude are applied to orthodontic appliances by loading of the associated arch wire and tie wings, and also during chewing.

Flexure strength indicates the ability for a ceramic material to withstand forces exerted during orthodontic treatment. Materials used in the orthodontic appliances of the present invention exhibit excellent flexure strength. Preferably, they possess a flexure strength of at least about 400 MPa (megapascals), more preferably at least about 500 MPa, and most preferably at least about 600 MPa. Having these strengths ensures that orthodontic appliances according to the invention are durable under typical use conditions.

The relatively high flexure strength of the appliances of the present invention is a significant advantage, because the overall size of the appliance as well as the size of protruding sections of the appliance (such as tie wings or hooks) can be reduced without significantly increasing the likelihood of breakage during use. Moreover, the increased strength enables the design and use of relatively complex shapes without fear of breakage. The resultant smaller size further increases the aesthetic appearance of the appliance because it is more difficult to see in the oral cavity. In addition, the smaller overall size reduces the likelihood that the appliance will contact opposing dentition, appliances mounted on opposing dentition or adjacent soft tissue.

Although the ceramic material used in an orthodontic appliance of the present invention is preferably at least about 99.5% pure (by weight), and more preferably at least about 99.9% pure, if desired, additives may be included in the ceramic material. These include dopants, colorants, and processing additives. Colorants can be used to achieve desired shades. Examples of suitable colorants include iron oxide, rare earth oxides, and bismuth oxide. Processing additives include, for example, sintering aids such as magnesium oxide, yttrium oxide, zirconium oxide, hafnium oxide, and calcium oxide. Various combinations of such additives can be used if desired. If used, such additives are present in an amount up to about 0.5 percent by weight (wt-%).

Methods of Making Ceramic Material

Various methods of shaping the ceramic material used in making the orthodontic appliances of the present invention may be employed, including die pressing, slurry casting, injection molding, extrusion processes, and rapid prototyping. The resultant material can be in the final desired shape or it can be partially in the form of an appliance (a "perform") that is subjected to further machining, for example. These processes are well known for their use in making ceramic materials.

Generally, a method for making a polycrystalline translucent aluminum oxide ceramic material as described herein includes: providing an aluminum oxide powder; forming the powder into an article having a desired shape; sintering the shaped article to obtain a sintered article having closed porosity; and subjecting the sintered article to hot isostatic pressing to further densify and form an orthodontic appliance or appliance preform that includes polycrystalline translucent aluminum oxide ceramic material.

In one embodiment, forming the powder into an article having a desired shape includes forming an appliance or appliance preform that includes ceramic material in a green stage. The green-stage appliance or appliance preform can be machined into a desired shape prior to sintering the shaped article. Alternatively, the sintered article (appliance) can be carved prior to subjecting it to hot isostatic pressing to further densify the article. Alternatively, the densified article (appliance) can be carved into a desired shape.

A preferred method of making the ceramic material used in making the orthodontic appliances of the present invention involves initially combining powdered aluminum oxide in water and treating to deagglomerate the particles. This treatment is preferably done using ultra-sonication. Typically, a sample of aluminum oxide is combined with water (generally distilled or deionized water) to form a slurry of about 25 wt-% to about 40 wt-% solids and sonicated for a period of time effective to deagglomerate the particles (typically about 1 hour to about 3 hours). If desired, the pH of the slurry can be adjusted for enhancing the dispersibility of the powder using, for example, ammonium citrate.

The aluminum oxide powder is preferably at least about 99.5% pure, more preferably at least about 99.9% pure, and most preferably at least about 99.99% pure. Typically, the powder includes particles having an average particle size (e.g., an average diameter) of no greater than about 0.5 micron and a surface area of greater than about 10 square meters per gram ($m^2/g$), preferably greater than about 14 $m^2/g$. Preferably, submicron size particles are used. This provides an active sintering process and allows one to achieve substantially theoretical density in the sintered, hot isostatic pressed compact.

This material is then typically combined with a small amount of a temporary organic binder, such as an acrylic binder or paraffin wax, optionally with a plasticizer such as polyethylene glycol, and then shaped. Preferably, about 5 weight percent (wt-%) to about 13 wt-% binder is applied by well-known methods (e.g., milling, spray drying) to the ceramic powder. Such binder is generally removed in subsequent processing operations. The mixture is typically then pressed into cylindrical pellets (typically of a diameter of about 10 mm to about 50 mm and a height of about 1 cm to about 100 cm) at room temperature under a pressure of about 100 MPa to about 350 MPa. Preferably, the pressed pellets are then subjected to cold isostatic pressing ("CIPing") at room temperature under a pressure of about 100 MPa to about 350 MPa. This material is typically referred to as the "green stage" of the material with binder and is relatively porous (e.g., at least about 25% porosity).

This green stage material is then heated under conditions to remove substantially all the organic binder. Typically, this occurs at a temperature of about 600° C. to about 700° C., preferably at atmospheric pressure, and for a time of about 1 hour to about 3 hours. After removal of the binder, the material is also often referred to as the "green stage." Preferably, the "green density" of the material at this stage is at least about 58% of full density.

This material is then subjected to heating (i.e., firing or sintering) to densify the material. Typically, heating involves a multi-step process. For example, the material can be sintered at a temperature of about 1200° C. to about 1300° C. in air for about 1 hour to about 3 hours. At this stage, the sintered material is preferably at about 96–98% of full density and generally has a bright white, opaque appearance.

This sintered material, which typically includes closed pores, may also then be heated under conditions to further densify the material and remove substantially all the pores. Typically, this occurs at a temperature of about 1200° C. to about 1450° C. for a time of about 1 hour to about 3 hours and typically results in a material of very low porosity. This final heating step preferably includes hot isostatic pressing ("HIPing") to accelerate the heating process and achieve full translucency. Isostatic pressure (provided by an inert gas, typically argon) is applied while the material is heated to the HIPing temperature. The combination of high temperature and high pressure compacts the material to have substantially zero porosity. U.S. Pat. No. 4,954,080 (Kelly et al.) provides further discussion as to hot isostatic pressing aluminum oxide. Preferred HIPing conditions include a temperature of about 1200° C. to about 1300° C. for about 30 minutes to about 120 minutes under about 100 MPa to about 210 MPa of an inert gas (e.g., argon). The aluminum oxide ceramic material is preferably fully sintered and HIPed to achieve greater than about 99.8% of the theoretical density of the ceramic material.

Significantly, the process of the present invention can be carried out in air or an inert gas without the use of any sintering additive. Sintering aids can be used, if desired, in an amount up to about 0.5 wt-% total. Examples of suitable sintering aids include magnesium oxide, yttrium oxide, zirconium oxide, hafnium oxide, and calcium oxide, which can be used in combination.

Orthodontic Appliances

The term "orthodontic appliance" is herein used in a broad sense to include any device intended for mounting on a tooth, and used to transmit to the tooth corrective force from an arch wire, spring, elastic, or other force-applying component. Examples of suitable appliances include brackets (including self-ligating brackets), buccal tubes, cleats and buttons. The term "arch-wire slot" is used broadly to designate any structure that receives or couples with the an arch wire.

FIG. 1 shows an exemplary orthodontic appliance in the form of an orthodontic bracket 10. The bracket has a base 11 suitable for either direct bonding to a tooth or attachment to any kind of mounting fixture. In instances where the base 11 is adapted for direct bonding to a tooth, a tooth-facing surface 12 of the base 11 is preferably conventionally concavely curved about both a mesiodistal axis and an apical axis to match the natural convexity of the tooth labial surface. However, other curvatures can be used to accommodate lingual bracket positioning.

A bracket body 13 extends from the base 11 to define bracket tie wings 14 for ligature anchorage, and a mesiodistally oriented arch-wire slot 15 extending from an outer body surface 16 into the bracket body. The presence or absence of tie wings (of either single-or twin-wing configuration) is not a feature of the invention, and the base and arch-wire slot may be angulated as desired to minimize or eliminate torquing or other bends of the arch wire.

A variety of other constructions are also possible. For example, the orthodontic appliance may include an arch wire slot liner, such as described in U.S. Pat. Nos. 5,380,196 (Kelly et al.) and 5,358,402 (Reed et al.). The appliance may also include a debonding channel as described in U.S. Pat. Nos. 5,439,379 (Hansen) and 5,380,196.

A preferred orthodontic appliance is made by pressing, sintering, and HIPing aluminum oxide as described above. The parts are preferably fabricated by pressing powder to a desired shape and sintering the pressed compact at temperatures such that the ceramic densifies.

In one such manufacturing technique, high purity aluminum oxide powder is placed in the die cavity of a high-pressure hydraulic press. The die has a cavity with a cross section corresponding to the desired cross section of the appliance being formed. The arch wire slot in the appliance may be completely or partially formed in this operation, or may be ground later. Undercuts beneath the tie wings are ground in later. A punch having the cross section of the die cavity is pressed into the powder in the cavity at about 70 MPa to about 140 MPa to tightly pack it. Optionally, a lateral slide is also employed for forming the curved base of the appliance. Such punches, dies, and slides are conventionally used for pressing a broad variety of metals or ceramics to desired shapes. Preferably, multiple die cavities are used in commercial operations for high productivity. Alternatively, such powder may be placed in a latex mold and isostatically pressed at about 140 MPa to about 310 MPa to form a green compact. In still another technique the green compact is made by "injection molding" the powder by conventional means at about 100 MPa.

A ceramic orthodontic appliance is secured to a tooth structure with an orthodontic adhesive substance. Good bonding of the adhesive to the base of the appliance is important so that it can withstand high occlusal forces and the stress of orthodontic correction. Controlled roughness of the base of the appliance may therefore be desirable to enhance bonding strength of the adhesive to the appliance.

As mentioned above, a polycrystalline ceramic orthodontic appliance may be made by compressing powder in a die. Preferably, a quantity of alumina particles such as small, irregular alumina shards are fixed to the base to enhance the bond between the appliance and the patient's tooth. The shards are secured to the base by first applying a glass frit to the base, then applying the shards to the frit, and then heating the assembly of the ceramic body, glass frit and shards in an oven. Once the glass softens, the shards become embedded in the glass and will remain securely connected to the base after the glass cools.

Other surfaces of the orthodontic appliance should be smooth. Optionally, smoothness is promoted by employing polished dies and punches in the pressing operation. The surfaces may be smoothed by grinding or by ultrasonic or abrasive polishing after sintering. Conventional flux polishing may also be used. In one such technique the appliance is immersed for up to thirty minutes in molten flux under conventional conditions.

The pressing and sintering technique for forming a polycrystalline ceramic article from ceramic powder can result in an orthodontic appliance with rather precise dimensions. Precision is enhanced by careful control of the pressing operation for forming green compacts and the mix of particle sizes in the ceramic powder. The sintering operation inherently causes shrinkage from the green compact to the finished article. The proportion of shrinkage can be known from carefully controlled particle size, mold geometry and pressure in green compact pressing. Care in these conventional techniques can produce finished orthodontic appliances well within acceptable tolerance limits. An important consideration on the orthodontic appliance is the archwire slot. If desired the slot may be ground into the appliance after pressing and sintering. Optionally, such grinding can be expedited by pressing in an undersized slot that is enlarged to the final desired configuration by grinding.

The orthodontic appliances of the present invention can be incorporated into a kit, wherein at least one of the appliances includes a polycrystalline translucent aluminum oxide ceramic material having an average grain size of no greater than 1.0 micron and a Contrast Ratio value of less than about 0.7. The kit can include one or more other components such as an orthodontic adhesive, an adhesive primer, an appliance positioning tool, and combinations thereof.

EXAMPLES

Objects and advantages of this invention are further illustrated by the following examples, but the particular materials and amounts thereof recited in these examples, as well as other conditions and details, should not be construed to unduly limit this invention. Unless otherwise indicated, all parts and percentages are by weight and all molecular weights are weight average molecular weight.

TEST METHODS

Hardness

The average microhardness of example materials was measured by mounting processed ceramic parts in mounting resin (obtained under the trade designation "EPOXIDE" from Buehler Ltd., Lake Bluff, Ill). More specifically, materials were secured in a 3.18-cm (1.25-inch) diameter, 1.9-cm (0.75-inch) tall cylinder of the resin. The mounted sample was polished using diamond lapping film (obtained under the trade designation "IMPERIAL DIAMOND LAPPING FILM" from the 3M Company, St. Paul, Minn.), with the final polishing step using a 0.5 micrometer diamond film to obtain polished cross-sections of the samples.

Hardness measurements were made using a conventional microhardness tester obtained under the trade designation "MITUTOYO MVK-VL" from Mitutoyo Corp. of Tokyo, Japan) fitted with a Vickers indenter using a 500-gram indent load. The hardness measurements were made according to the guidelines stated in ASTM Test Method E384 Test Methods for Microhardness of Materials (1991). The reported hardness values are an average of 10 measurements.

Flexure Strength

Test bars measuring 2.5-mm wide×1.5-mm thick×12.0-mm long, with 0.15±0.05 mm×45° chamfers, were machined by Chand Kare Technical Ceramics, Worcester, Mass. The test bars were soaked in distilled water at 37° C. for 24 hours prior to testing. A 3-point beam bend test configuration with a span of 10.0 mm was employed. The crosshead test speed was 0.75 mm/min. An Instron 4505 test frame (Instron Corporation, Canton, Mass.) was utilized. Flexure Strength results were reported in units of MPa as minimum, maximum, and average strength values. Average strength values are an average of 5 measurements.

Contrast Ratio

In order to quantitatively assess translucency of a material, ceramic discs with 2 parallel flat surfaces, a thickness of 1.0±0.03 mm, and various diameters ranging from 12 to 15 mm were prepared by cutting discs at a speed of 2500 rpm and a load of 1000 grams using a Buehler Isomet 2000 Precision Saw (Buehler Co., Lake Bluff, Ill.) and a Buehler Series 15-LC diamond wafering blade (15.24 cm, #11-4276). Both surfaces (front and back of disc) were made uniform by passing them back and forth 10 times over an approximately 7.6-cm path along 600-grit sandpaper (3M Wetordry Tri-M-Ite, #438Q; 3M Company, St. Paul, Minn.). Distilled water was used as a lubricant and to rinse the sample discs.

ASTM-D2805-95 test method was modified to measure the Contrast Ratio (or opacity) of the discs. Y-tristimulus values for the discs were measured on an Ultrascan XE Colorimeter (Hunter Associates Laboratory, Reston, Va.) with a 0.953-cm aperture using separate white and black backgrounds. The D65 Illuminant was used with no filters for all measurements. A 10° angle of view was used. The Contrast Ratio or opacity, C, was calculated as the ratio of the reflectance through a material on a black substrate to that of an identical material on a white substrate. Reflectance is defined as equal to the Y-tristimulus value. Thus, C=RB/RW, where RB=reflectance through a ceramic disc on a black substrate and RW=reflectance through the same disc on a white substrate. Reported Contrast Ratio values are the results of single measurements. Lower values are indicative of greater translucency (i.e., transmission of light).

Translucency of Small Samples (Wet Transmittance)

The translucency of small test samples, e.g., the size of an orthodontic bracket, was quantitatively measured according to the following method that is a modification of the published standard method, "Materials and Articles in Contact with Foodstuffs: Test Methods for Translucency of Ceramic Articles"; DIN EN 1184; August, 1997. Small test samples, for example ceramic orthodontic brackets, were cleaned with ethanol, and dried in a stream of anhydrous nitrogen. The dried samples were sputter coated with approximately 40 nm of Au/Pd, and mounted into 2.54-cm phenolic rings using Buehler-Two Part Epoxy (Buehler Co., Lake Bluff, Ill.). Special attention was paid to the mounting orientation of the samples to ensure that a representative cross-section of the sample would be created, and that any non-alumina materials (such as glass frit coatings) would be removed during the sectioning process. The mounts were allowed to cure overnight at room temperature. The cured mounts were sectioned to between approximately 1.5 to 5-mm widths with a Struers Accutom-50 high-speed diamond saw.

Following sectioning, samples were hand ground on 600-grit SiC grinding paper on a Buehler Ecomet 4 (Buehler Co., Lake Bluff, Ill.). A Fowler micrometer caliper was used to monitor progress of material removal. Once samples were ground to within approximately 20–30% of ideal width (1000 $\mu$m), samples were polished using 3M Imperial Diamond Lapping Film (9 $\mu$m) placed on a flat table. Small amounts of water and Buehler Metadi Fluid (diamond extender) were used as lubricants for the grinding and polishing steps. Final widths of all samples through the plane of interest were 1000 $\mu$m (+/−2%).

The test procedure used was based on DIN EN 1184—1997 "Materials and articles in contact with foodstuffs: Test methods for translucency of ceramic articles," (August, 1997). This DIN standard procedure was modified as follows:

Section 4.2.1 Photometer—a spectrophotometer rather than a photometer was used. Visible light microspectrophotometry was done using a Leica Orthoplan Microscope, an 16X/0.30NA objective, 0.30 substage condenser, and a Leica MPV-Combi spectrophotometer.

Section 4.3 Preparation of test specimen. For the data reported herein, the specimens were 1.00-mm thick rather than 2.00-mm thick.

Measurements were made for each sample by utilizing the 16X/0.30NA objective to produce a light source with a half angle of 17 degrees. A "wet" reading was taken by submerging (in immersion oil) each sample in a well slide. This well slide was made by the 3M Glass Shop and consisted of a standard microscope slide with 0.6-cm glass cylinder attached to create a flat bottom well. The operating conditions of the Leica MPV were: scan range of 350 nm to 800 nm, 2X integration, 300-hz filter edge, and 4 scan averaging. Four locations on the polished bracket were scanned (4 scans at each location) and the results were averaged in the reported data. The system was calibrated following the manufacturers instructions. The calibration condition for 100% transmission was defined as the well slide filled with immersion oil.

Grain Size

The average grain size of an alumina test sample was determined from Scanning Electron Microscopy (SEM) images. Prior to scanning, the sample was mounted and polished as described above for hardness testing. Following polishing, the sample was removed from the mounting media, cleaned and immersed for 1 minute in an aqueous supersaturated borax (sodium borate) solution at 80° C. The sample, coated with the sodium borate solution, was then heated at 5° C./min to 900° C. and soaked at 900° C. for 30 minutes in flowing air. The borax solution reacted with the alumina to form a glass at the polished surface grain boundaries. Upon cooling, the polished surface was etched for 1 minute in a boiling 12% HCl acid solution to remove the resultant glass. This procedure served to reveal the grain structure of the sample without doing a higher temperature thermal etch that might have altered the existing microstructure.

Following rinsing with deionized water and drying in air, the sample was mounted on aluminum SEM stubs and coated with a thin layer of Au/Pd. The samples were viewed at an angle normal to the polished surface using a scanning electron microscope (obtained under the trade designation "JEOL Model JSM 6400" from JEOL, Ltd. of Akishima, Japan). The average grain size of the sample was determined using the linear-intercept method on the plane of polish as described by M. I. Mendelson, "Average Grain Size in Polycrystalline Ceramics," *Journal of the American Ceramic Society*, 52 [8] 443–446 (1969), using a proportionality constant (k) of 1.56, which relates the average grain size (D) to the average intercept length (L): D=1.56 L.

Starting Materials

Alumina Powder

Starting alumina ($Al_2O_3$) powder was obtained from Taimei Chemicals Co., Tokyo, Japan and designated TM-DAR. The powder was reported by the manufacturer to have a nominal composition of 99.99 wt-% $Al_2O_3$, with the balance being comprised of impurities of the following metals/oxides: Na (5 ppm), K (1 ppm), Fe (4 ppm), Ca (1 ppm), Mg (1 ppm) and Si (2 ppm). The nominal surface area of this powder was 14.8 $m^2/g$ with an average particle size of 0.18 μm (manufacturer's data).

Example 1 Polycrystalline Translucent Alumina Preparation

Initial Alumina Powder Treatment

The TM-DAR alumina powder as received was de-agglomerated and prepared for subsequent processing as follows. The powder was mixed with distilled water (in an amount equal to approximately 42% by weight of the powder) and ammonium hydrogen citrate powder (Sigma-Aldrich Chemical Company, St. Louis, Mo.) (in an amount equal to approximately 0.45% by weight of the powder) in a polyethylene bottle. The bottle was placed in an ultrasonic water bath at room temperature and the powder slurry was ultrasonicated for 2 hours. Following sonication, ammonium hydroxide (Alfa Aesar, Ward Hill, Mass.) was added in an amount equal to approximately 0.3% by weight of the powder to raise the pH of the solution. The resulting slurry was then further prepared for spray drying by adding DURAMAX B-1000 binder, an acrylic resin manufactured by Rohm and Haas Company, (Philadelphia, Pa.). Prior to adding the binder (in an amount equal to approximately 9.7% by weight of the powder), the binder was diluted with approximately 2 parts distilled water to 1 part binder. Next, Carbowax Polyethylene Glycol 400, a plasticizer from Union Carbide, (Danbury, Conn.) was added to the slurry in an amount equal to approximately 1.1% by weight of the powder. Prior to adding the Carbowax 400 to the powder-binder slurry, the Carbowax 400 was diluted with approximately 4.5 parts distilled water to 1 part Carbowax 400. The resulting slurry was mixed with a magnetic stirbar and spray dried (Buchi Mini Spray Dryer B-191, obtained from Brinkman Instruments, Westbury, N.Y.; Inlet Temperature=195° C., Outlet Temperature=100° C.) to produce a fine, free-flowing powder suitable for further processing.

Powder Formation Processing

The free-flowing alumina powder was uniaxially pressed into 10.25-g cylindrical pellets by using a die with a diameter of 16.6 mm and an applied pressure of approximately 310 MPa. (Press was obtained from Carver Laboratory Press, Model M, Carver, Inc., Wabash, Ind.). The resulting pellets were then cold isostatically pressed (CIPed) at approximately 170 MPa (Model #IP4-22-60, Autoclave Engineers, Erie, Pa.).

Binder Burn-out Processing

The CIPed pellets (or ceramic parts of other shapes) were burned out in air at 690° C. for 1 hour to remove the organic components added to facilitate dispersion and spray drying. (The ramp rate to 690° C. was approximately 1° C./min. After a 1 hour soak at 690° C., the furnace power was shut-off and the furnace cooled at its own rate.) Following binder burnout, the ceramic parts typically had a "green" (non-sintered) density in excess of 58% (on a theoretical density basis of 3.98 $g/cm^3$).

Sintering Processing

Figure 2:
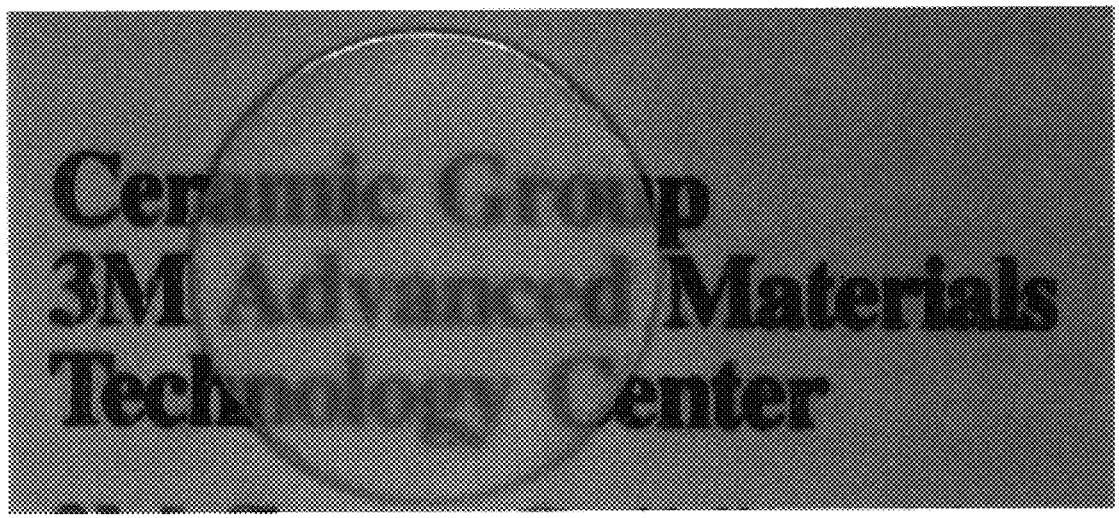
FIG. 2 depicts a qualitative translucency assessment of Example 1 ceramic material.
Figure 3:
FIG. 3 is a Scanning Electron Microscopy (SEM) image (2000x) of a cross-section of the Example 1 ceramic material.

Following binder burn-out processing, the ceramic parts were sintered at 1235° C. in air for 2 hours with ramp and cool rates of 2°° C./min. This pressureless, sintering process typically produced ceramic parts having a density of approximately 3.83 $g/cm^3$, approximately 96% of their theoretical density. At approximately 96% of full density, these ceramic parts were bright white and opaque in appearance. Additionally, the ceramic parts had reached closed porosity at this point in the process, as indicated by near equivalence in their dry weights and saturated weights as determined by the Archimedes density technique Once closed porosity was reached, the sintered ceramic parts were capable of being hot isostatically pressed (HIPed) without encapsulation Hot Isostatically Pressed Powder Processing The sintered ceramic parts were HIPed at 1275° C. for 65 minutes with an applied argon pressure of 207 MPa and heating ramp rates of 20° C./min below 1200° C. and 13° C./min above 1200° C. The cooling rate was approximately 25° C./min. The resulting ceramic parts (Example 1 Translucent Alumina) had a final density of approximately 3.98 $g/cm^3$ (essentially 100% of its theoretical density, based on atomic packing considerations) and were translucent in appearance. A qualitative assessment of Example 1 translucency was made as shown in FIG. 2, demonstrating that printed text could readily be read through a 1-mm thick disc of the material. The average grain size of the Example 1 Alumina was measured according to the test method provided herein and was determined to be 0.8 µm. A Scanning Electron Microscopy (SEM) image (2,000x) of the Example 1 Alumina is shown in FIG. 3. The hardness of the Example 1 Alumina was measured according to the test method provided herein and was found to be 22.1±0.5 GPa.

Example 2 Polycrystalline Translucent Alumina Preparation

Figure 4:
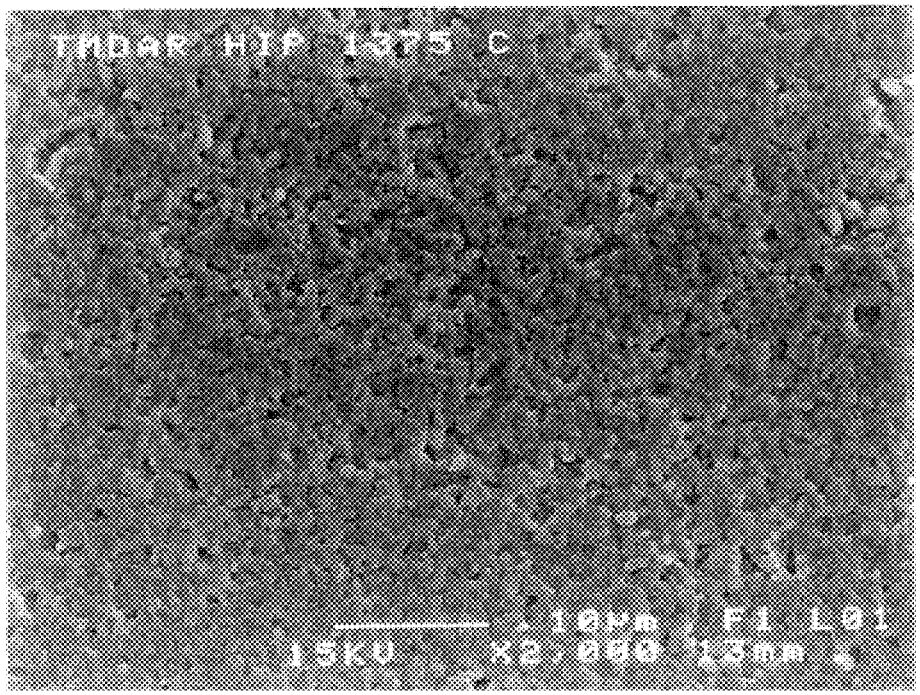
FIG. 4 is an SEM image (2,000x) of a cross-section of the Example 2 ceramic material.

The TM-DAR alumina powder was processed as described for Example 1, except that the sintered pellets (or ceramic parts) were HIPed at 1375° C. (as compared to 1275° C. in Example 1) for 30 minutes (as compared to 65 minutes in Example 1). The resulting ceramic parts (Example 2 Translucent Alumina) had a final density of approximately 3.99 g/cm$^3$ (slightly greater than 100% of what was believed to be its theoretical density) and were translucent in appearance, appearing visually to be of a similar translucency to Example 1 Alumina. The average grain size of the Example 2 Alumina was measured according to the test method provided herein and determined to be 0.9 µm. A Scanning Electron Microscopy image (2,000x) is shown in FIG. 4. The hardness of the Example 2 Alumina was measured according to the test method provided herein and was found to be 21.7±0.7 GPa.

Example 3 Polycrystalline Translucent Alumina Preparation

In order to prepare larger quantities of the polycrystalline translucent alumina and to ensure that all parts were uniformly processed, the following modified process was employed.

The TM-DAR alumina powder as received was processed as described for Example 1, except that the binder burn-out at 690° C. was extended to 2 hours (from 1 hour) and the pressureless, sintering temperature was raised to 1250° C. (from 1235° C.) to ensure that all ceramic parts reached closed porosity prior to subsequent HIPing. It is believed that the ceramic parts and physical properties produced under these modified conditions do not differ appreciably from those described in Example 1. Rather, it is believed that it is the typical scale-up, "mass" effects (e.g., air flow and/or thermal effects) that require the extension of burn-out time and the increase in sintering temperature to ensure uniform processing results.

Properties and additional characterization of Example 3 Translucent Alumina are included below.

In order to compare the translucent alumina materials of this invention with commercially available translucent and opaque aluminas, the following comparative examples were characterized as described below.

Comparative Example A

Figure 5:
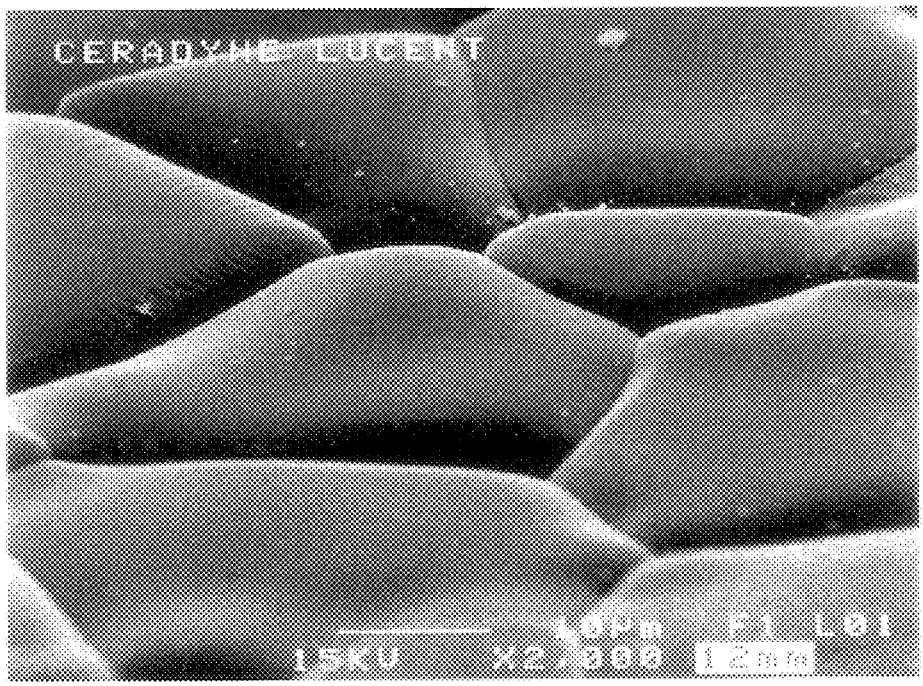
FIG. 5 is an SEM image (2,000x) of a cross-section of the Comparative Example A ceramic material.

Comparative Example A is a translucent alumina available from Ceradyne, Inc., Costa Mesa, Cali., and sold under the tradename TRANSTAR. The grain size of the TRANSTAR ceramic was measured according to the test method provided herein and found to be 30.0 microns. The hardness of the TRANSTAR ceramic was measured according to the test method provided herein and found to be 19.7±0.8 GPa. A Scanning Electron Microscopy image (2,000x) of Comparative Example A is shown in FIG. 5.

Comparative Example B

Comparative Example B is an opaque (ivory-colored) alumina, available under the trade designation of "998" from Vesuvius McDanel, Beaver Falls, Pa.

Comparative Example C

Comparative Example C is translucent alumina available from Ceradyne, Inc., and sold under the tradename "CERA-DYNE TPA." This material is used to produce the 3M CLARITY line of orthodontic brackets (3M Unitek, Monrovia, Cali.).

Comparative Example D

Comparative Example D is a commercially available translucent alumina orthodontic bracket, available under the trade designation of "CONTOUR Ceramic Brackets" from Class One Orthodontics, Lubbock, Tex.

Comparative Example E

Comparative Example E is a commercially available translucent alumina orthodontic bracket, available under the trade designation of "MXi" from TP Orthodontics, Inc., LaPorte, Ind.

Test Evaluations and Results

In order to compare the fine-grained translucent alumina materials of the present invention with other commercially available aluminas, the characterization outlined below was completed. This work compared the translucent alumina of the present invention to both coarse-and fine-grained translucent alumina as well as to coarse-grained opaque alumina.

Flexure Strength

Flexure Strength was measured according to the Test Method described herein and the test results for Example 1 and Comparative Examples A and B are reported in Table 1.

TABLE 1

| | Flexure Strength | | |
|---|---|---|---|
| Sample | Average Strength MPa (Standard Deviation) | Maximum Strength MPa | Minimum Strength MPa |
| Example 1 | 620 (161) | 817 | 366 |
| Comparative Ex. A | 280 (32) | 321 | 234 |
| Comparative Ex. B | 340 (24) | 377 | 310 |

The results in Table 1 indicate that the Flexure Strength of the Example 1 translucent alumina is approximately 2 times that of the Comparative Example A translucent material. It should be noted that the large standard deviation in the Example 1 values likely resulted from the difficulties experienced in machining this material. The fine-grained structure and high strength/hardness made defect-free machining of Example 1 flexure bars very challenging. However, the demonstrated strength of Example 1 may allow smaller, less bulky translucent orthodontic brackets to be constructed from such material.

Translucency: Contrast Ratio

In order to quantitatively assess the translucency of ceramic samples, Contrast Ratio was measured according to the Test Method described herein and the test results for Example 3, and Comparative Examples A and B are reported in Table 2.

TABLE 2

Translucency

| Sample | Contrast Ratio |
| --- | --- |
| Example 3 | 0.307 |
| Comparative Ex. A | 0.513 |
| Comparative Ex. B | 0.983 |

The results in Table 2 indicate that the translucency of the Example 3 Alumina exceeds that of the Comparative Example A material and thus would be very suitable for highly aesthetic dental articles, e.g., dental prostheses or orthodontic brackets, that allow natural tooth color to diffusely show through the article. This result was surprising in that it had been previously reported (e.g., U.S. Pat. No. 4,954,080) that if the average grain size of a ceramic appliance was less than about two microns, then optical effects due to adjacent grain boundaries might interfere with good light transmission through the appliance.

Hardness and Grain Size Comparison of Ceramic Samples

Figure 6A:
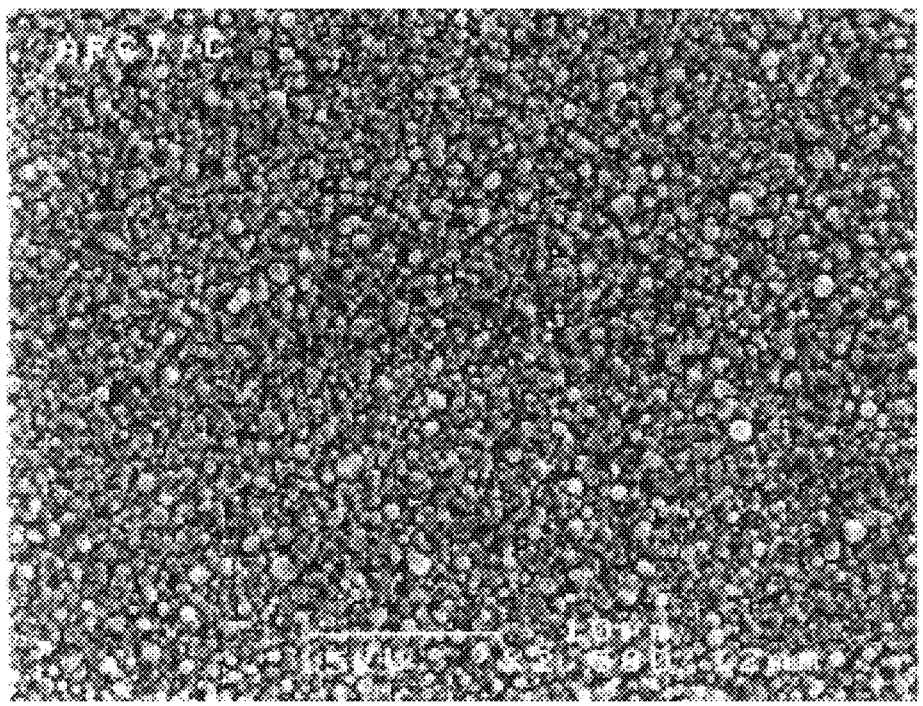
FIG. 6a is an SEM image (2,500x) of a cross-section of the Example 3 ceramic material.
Figure 6B:
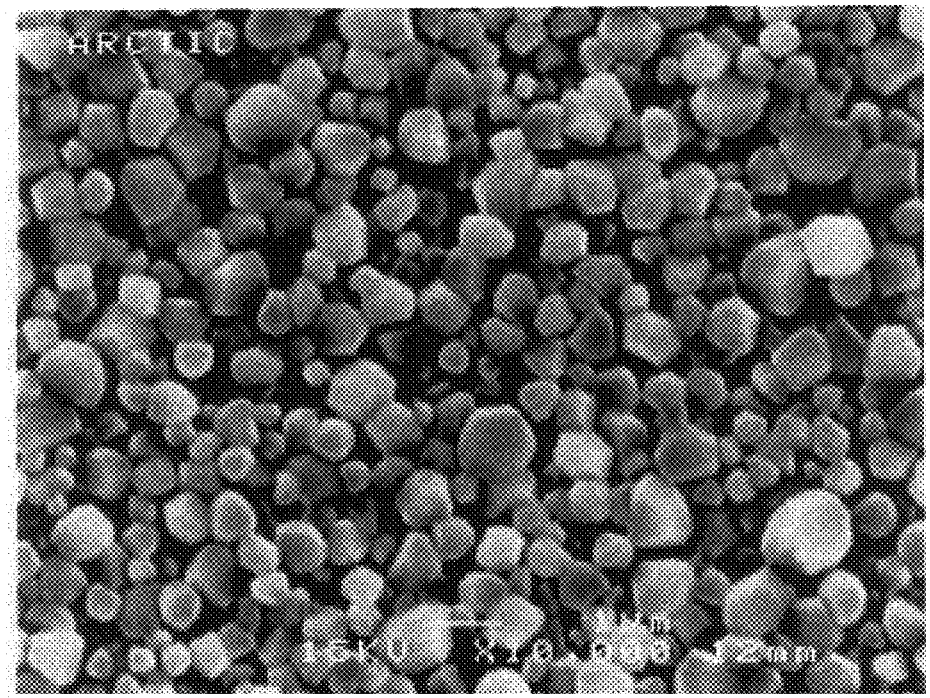
FIG. 6b is an SEM image (10,000x) of a cross-section of the Example 3 ceramic material.
Figure 7:
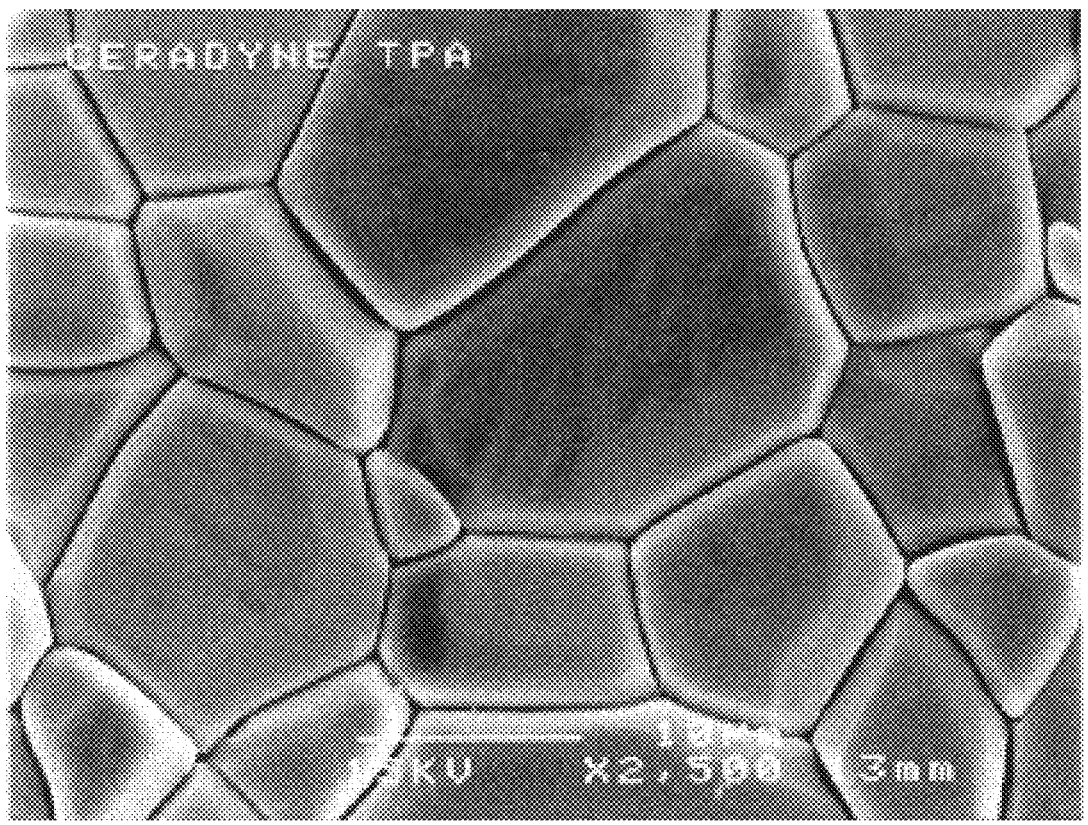
FIG. 7 is an SEM image (2,500x) of a cross-section of the Comparative Example C ceramic material.
Figure 8A:
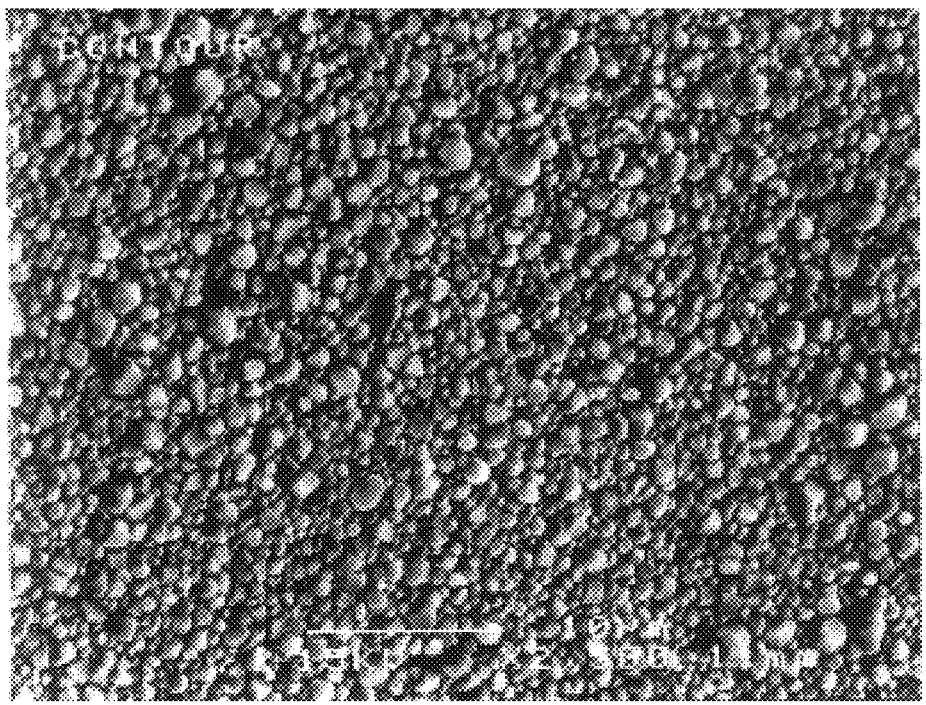
FIG. 8a is an SEM image (2,500x) of a cross-section of the Comparative Example D ceramic material.
Figure 8B:
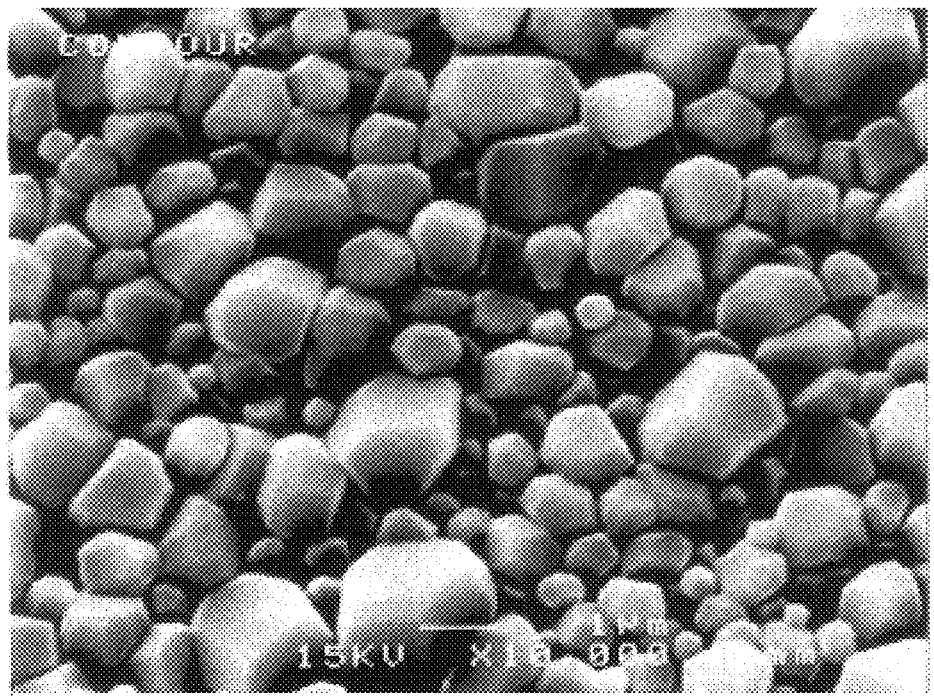
FIG. 8b is an SEM image (10,000x) of a cross-section of the Comparative Example D ceramic material.
Figure 9A:
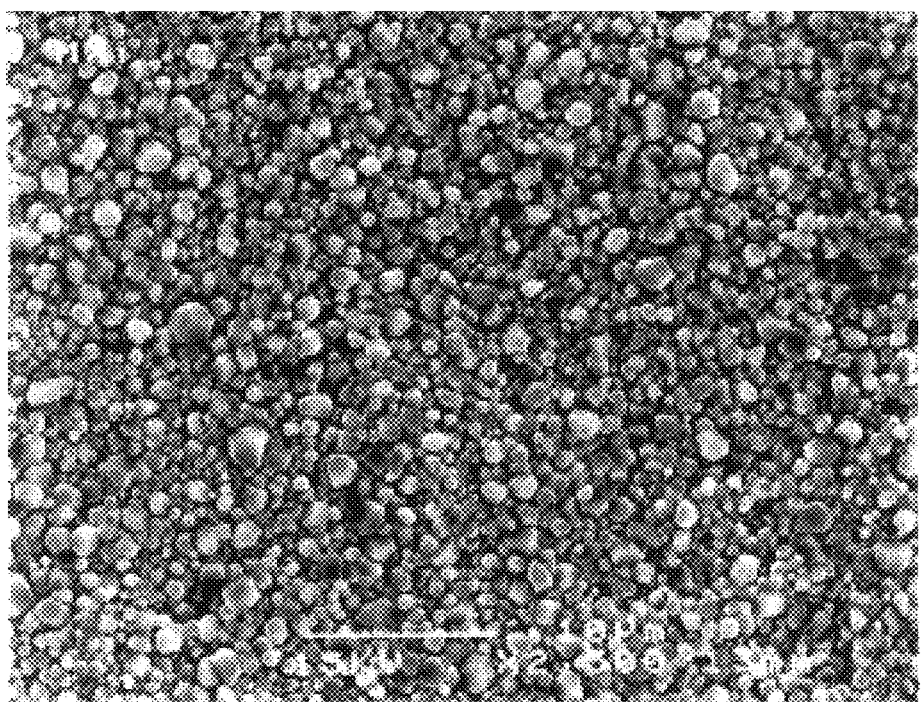
FIG. 9a is an SEM image (2,500x) of a cross-section of the Comparative Example E ceramic material.
Figure 9B:
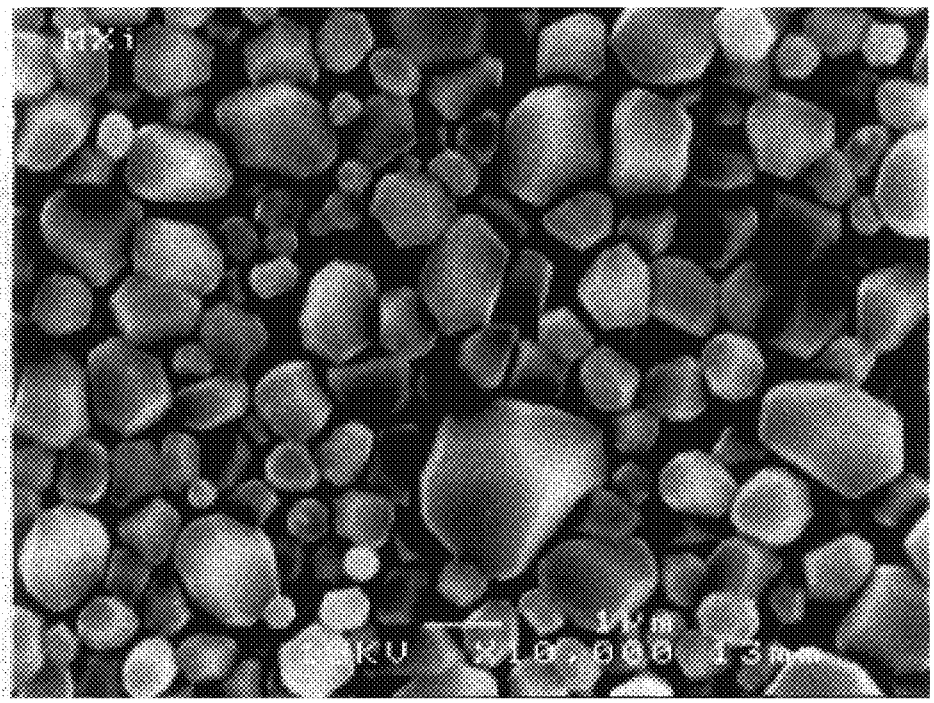
FIG. 9b is an SEM image (10,000x) of a cross-section of the Comparative Example E ceramic material.

Hardness and Grain Size were determined according to the Test Methods described herein and the results for Example 3, Comparative Example C, and the two bracket samples (Comparative Examples D and E) are reported in Table 3. Examples of the SEM images (2,500x and 10,000x) used to determine the average grain sizes of the Example 3, Comparative Example C, Comparative Example D, and Comparative Example E samples are shown in FIGS. 6a and 6b, FIG. 7 (2500x only), FIGS. 8a and 8b, and FIGS. 9a and 9b, respectively.

TABLE 3

Hardness and Grain Size of Ceramic Samples

| Bracket Sample | Hardness (GPa) | Grain Size (Microns) |
| --- | --- | --- |
| Example 3 | 20.9 ± 0.8 | 0.8 |
| Comparative Ex. C | 17.1 ± 0.6 | 15.3 |
| Comparative Ex. D | 20.5 ± 0.5 | 1.3 |
| Comparative Ex. E | 20.0 ± 0.5 | 1.2 |

The results in Table 3 indicate that the hardness of the Example 3, Comparative Example D, and Comparative Example E samples are statistically equivalent and that all three of these "fine-grained" samples have larger hardness values (and therefore may be expected to be stronger) than the "coarser-grained" Comparative Example C sample. The average grain size of the Comparative Example C sample was about 18 times larger than the Example 3 sample. The average grain sizes of the Comparative Example D and E samples were similar and about 50% larger than the Example 3 sample. Additionally, it is clear from the SEM images (FIGS. 6a, 6b, 8a, 8b, 9a, and 9b) that the Example 3 grains appeared visually to be more uniform or unimodal in size, while the Comparative Example D and E samples had a broader, distribution of grain sizes, with a greater number of larger single grains. Because of the smaller and more uniform grain composition of the Example 3 sample, articles constructed from this material would be expected to have improved physical and mechanical properties.

It should be noted that grain sizes different than those stated above for the Comparative Examples D and E materials have been previously reported (Giao (Robert) Ngoc Pham, "Fracture Characteristics, Hardness, and Grain Size of Five Polycrystalline Alumina Orthodontic Brackets," Ohio State University Master's thesis, 1999). In that report Pham states that the "grain size" of Comparative Example D (CONTOUR) is 0.57 microns and that the "grain size" of Comparative Example E (MXi) is 0.65 microns. However, both Pham and the reference he cites describing his "grain size" measurement technique, (L. H. VanVlack, "Elements of Materials Science and Engineering," $6^{th}$ Edition, 217–219, 1989) state, "The mean chord length, L, is an index of grain size." As noted above, this mean chord or intercept length must be multiplied by a proportionality constant to determine an actual grain size. However, Pham goes on to report this index of grain size (chord length) as the actual grain size, without multiplying by the needed proportionality constant. Furthermore, the VanVlack reference states that L is determined "by placing a random line of known length across a polished and etched microstructure," as was done in the technique described herein. However, Pham states, "Brackets of each brand were then notched with a diamond disk and fractured with a chisel. These fractured bracket halves were also mounted and coated with a gold-palladium film. The fracture surface morphology of each bracket was observed, and representative SEM photomicrographs were taken. The mean grain sizes of the five polycrystalline brackets were calculated directly from the SEM photomicrographs using a modified intercept method." The differences between examining a polished surface (as called for in the referenced standard) and a fractured surface (as Pham did), as well as Pham's failure to apply the proportionality constant, likely lead to the discrepancies in reported grain size for Comparative Examples D and E herein and in Pham's report.

Translucency: Bracket-Sized Samples

Figure 10:
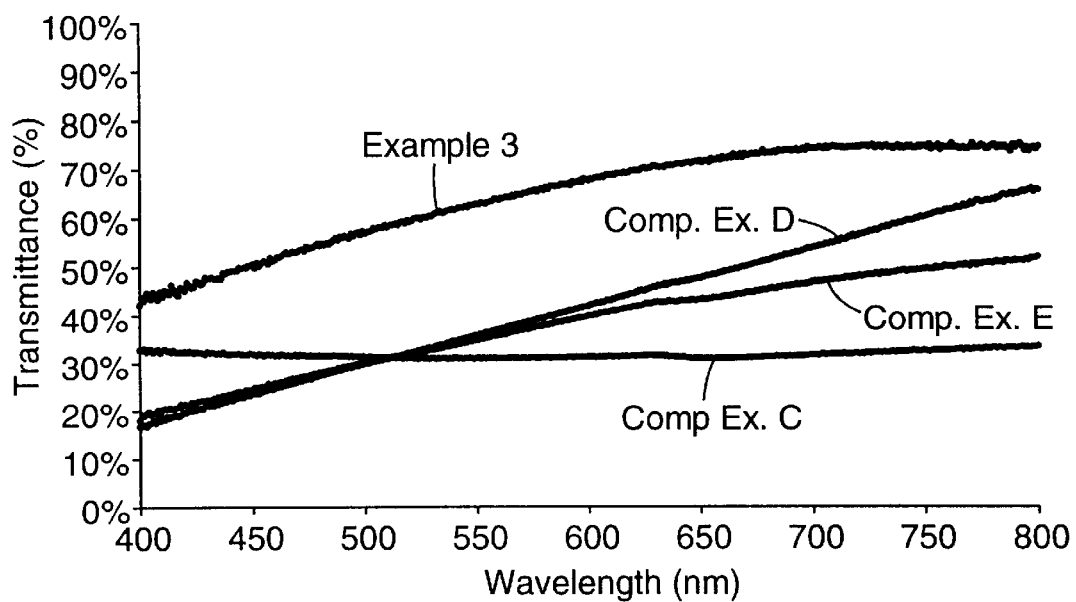
FIG. 10 is a graphical representation of Light Transmittance (%) versus Wavelength (nm) for Example 3, Comparative Example C, Comparative Example D, and Comparative Example E ceramic materials.

Translucency was determined according to the "Translucency of Small Samples (Wet Transmittance)" Test Method described herein and the results for Example 3, and Comparative Examples C, D and E are reported in tabular form (Table 4) as well as in graphical form (FIG. 10).

TABLE 4

Translucency of Bracket-Sized Samples

| Bracket Sample | Wet Transmittance (%) | Wavelength (nm) |
| --- | --- | --- |
| Example 3 | 42 | 400 |
|  | 57 | 500 |
|  | 68 | 600 |
|  | 74 | 700 |
|  | 75 | 800 |
| Comparative Ex. C | 33 | 400 |
|  | 31 | 500 |
|  | 31 | 600 |
|  | 32 | 700 |
|  | 34 | 800 |
| Comparative Ex. D | 17 | 400 |
|  | 30 | 500 |
|  | 42 | 600 |
|  | 54 | 700 |
|  | 66 | 800 |
| Comparative Ex. E | 18 | 400 |
|  | 30 | 500 |
|  | 40 | 600 |
|  | 47 | 700 |
|  | 52 | 800 |

The results in Table 4 and FIG. 10 indicate that the Example 3 sample is appreciably more translucent than the other three materials. The wet transmittance of the Example 3 sample is about 2 times greater than the wet transmittance of Comparative Example D and E samples at lower wavelengths and 25–5% greater at longer wavelengths. The integrated area under a wet transmittance vs wavelength curve, another measure of the translucency of these materials, is reported in Table 5 (in units of Percent Wet Transmittance×Light Wavelength (nm) or % T-nm).

TABLE 5

Integrated Translucency (between 475 and 650 nm)

| Sample | Integrated Wet Transmittance (% T-nm) |
|---|---|
| Example 3 | 110 |
| Comparative Example C | 55 |
| Comparative Example D | 65 |
| Comparative Example E | 62 |

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. An orthodontic appliance comprising a polycrystalline translucent aluminum oxide ceramic material having an average grain size of no greater than 1.0 micron and a Contrast Ratio value of less than about 0.7.

2. The orthodontic appliance of claim 1 wherein the appliance is attached to a tooth structure with an orthodontic adhesive.

3. The orthodontic appliance of claim 1 wherein no greater than 10% of the grains of a polished surface of the ceramic material has a largest dimension greater than 1.0 micron.

4. The orthodontic appliance of claim 1 wherein the ceramic material has a wet transmittance of at least about 40% at about 550 nm.

5. The orthodontic appliance of claim 4 wherein the ceramic material has a wet transmittance of at least about 50% at about 650 nm.

6. The orthodontic appliance of claim 1 wherein a wet transmittance curve of the ceramic material over a range of about 475 nm to about 650 nm has an integrated area of greater than about 70% T-nm.

7. The orthodontic appliance of claim 1 wherein the ceramic material has a Contrast Ratio value of less than about 0.5.

8. The orthodontic appliance of claim 7 wherein the ceramic material has a Contrast Ratio value of less than about 0.4.

9. The orthodontic appliance of claim 1 wherein the ceramic material has a flexure strength of at least about 400 MPa.

10. The orthodontic appliance of claim 9 wherein the ceramic material has a flexure strength of at least about 600 MPa.

11. The orthodontic appliance of claim 1 wherein the ceramic material has a purity of at least about 99.5 wt-%.

12. The orthodontic appliance of claim 11 wherein the ceramic material comprises up to about 0.5 wt-% of magnesium oxide, yttrium oxide, zirconium oxide, hafnium oxide, calcium oxide, or combinations thereof.

13. The orthodontic appliance of claim 1 wherein the appliance includes a base, and further including an adhesive applied to the base.

14. A kit comprising a plurality of orthodontic appliances, wherein at least one of the appliances comprise a polycrystalline translucent aluminum oxide ceramic material having an average grain size of no greater than 1.0 micron and a Contrast Ratio value of less than about 0.7.

15. The kit of claim 14 further comprising a component selected from the group consisting of an orthodontic adhesive, an adhesive primer, an appliance positioning tool, and combinations thereof.

16. The kit of claim 15 wherein each appliance includes a base, and wherein the kit additionally includes an orthodontic adhesive applied to the base of one or more appliances.

* * * * *

UNITED STATES PATENT AND TRADEMARK OFFICE
CERTIFICATE OF CORRECTION

PATENT NO. : 6,648,638 B2
DATED : November 18, 2003
INVENTOR(S) : Castro, Darren T.

It is certified that error appears in the above-identified patent and that said Letters Patent is hereby corrected as shown below:

Column 2,
Line 8, "effecting" should be -- affecting --.
Lines 28 and 37, "perform" should be -- preform --.

Column 6,
Line 4, "perform" should be -- preform --.

Column 7,
Line 50, delete "the" preceding "an".
Line 66, "single-or" should be -- single- or --.

Column 12,
Lines 33 and 44, "Bum-out" and "bum-out" should be -- Burn-out -- and -- burn-out -- respectively.
Line 46, "2°° C./min" should be -- 20° C./min. --

Column 16,
Line 65, "25-5%" should be -- 25-50% --.

Signed and Sealed this

Eleventh Day of May, 2004

JON W. DUDAS
*Acting Director of the United States Patent and Trademark Office*

UNITED STATES PATENT AND TRADEMARK OFFICE
CERTIFICATE OF CORRECTION

| | |
|---|---|
| PATENT NO. | : 6,648,638 B2 |
| APPLICATION NO. | : 10/034997 |
| DATED | : November 18, 2003 |
| INVENTOR(S) | : Castro et al. |

It is certified that error appears in the above-identified patent and that said Letters Patent is hereby corrected as shown below:

Title Page, item (56) References Cited:

U.S. Patent Documents, page 2, line 3, delete "1/1969" insert --8/1967--.
line 4, delete "9/1969" insert --10/1964--.

Foreign Patent Documents, insert --DE 2 039 226 3/1971-- following "DE 1 541 219 1/1970".

Signed and Sealed this

Twenty-eighth Day of August, 2007

JON W. DUDAS
*Director of the United States Patent and Trademark Office*